(12) United States Patent
Chaouk et al.

(10) Patent No.: US 7,666,339 B2
(45) Date of Patent: Feb. 23, 2010

(54) HYDROGEL STRING MEDICAL DEVICE

(75) Inventors: Hassan Chaouk, Smyrna, GA (US); Bruktawit T. Asfaw, Norcross, GA (US)

(73) Assignee: Bio Cure, Inc., Norcross, GA (US)

( * ) Notice: Subject to any disclaimer, the term of this patent is extended or adjusted under 35 U.S.C. 154(b) by 230 days.

(21) Appl. No.: 11/368,240

(22) Filed: Mar. 3, 2006

(65) Prior Publication Data
US 2006/0147483 A1    Jul. 6, 2006

Related U.S. Application Data

(63) Continuation of application No. 10/809,140, filed on Mar. 25, 2004, now abandoned.

(60) Provisional application No. 60/457,735, filed on Mar. 25, 2003.

(51) Int. Cl.
*A61M 25/14* (2006.01)
*A61M 36/06* (2006.01)

(52) U.S. Cl. ............... 264/211.24; 604/508; 264/176.1; 425/462

(58) Field of Classification Search ............ 264/211.24; 604/508, 515, 506, 507; 425/462
See application file for complete search history.

(56) References Cited

U.S. PATENT DOCUMENTS

| | | | |
|---|---|---|---|
| 5,443,454 A * | 8/1995 | Tanabe et al. ............... 604/264 |
| 5,508,317 A | 4/1996 | Mueller | |
| 5,833,652 A | 11/1998 | Preisman | |
| 5,976,186 A * | 11/1999 | Bao et al. ............... 623/17.16 |
| 6,139,520 A | 10/2000 | McCrory | |
| 6,140,452 A | 10/2000 | Felt et al. | |
| 6,152,943 A * | 11/2000 | Sawhney ............ 606/193 |
| 6,299,590 B1 | 10/2001 | Luscher | |
| 6,312,421 B1 | 11/2001 | Boock | |
| 6,558,367 B1 | 5/2003 | Cragg | |
| 2001/0036451 A1* | 11/2001 | Goupil et al. ............ 424/78.38 |

FOREIGN PATENT DOCUMENTS

| | | |
|---|---|---|
| WO | WO 97/22372 | 6/1997 |
| WO | WO 00/09190 | 2/2000 |
| WO | WO 00/18469 | 4/2000 |
| WO | WO 00/50103 | 8/2000 |
| WO | WO 00/64977 | 11/2000 |
| WO | WO 02/089679 | 11/2002 |

OTHER PUBLICATIONS

Encyclopedia of Polymer Science and Engineering, vol. 4, John Wiley & Sons, (1986) pp. 519-524.*

* cited by examiner

*Primary Examiner*—Matthew J. Daniels
(74) *Attorney, Agent, or Firm*—Collen A. Beard

(57) ABSTRACT

A hydrogel string that is useful as a medical device and a method for forming a hydrogel string that utilizes a delivery device in which gelation of a prepolymer is initiated to form a hydrogel, which is then extruded from the device as the hydrogel string.

8 Claims, 1 Drawing Sheet

HYDROGEL STRING MEDICAL DEVICE

CROSS-REFERENCE TO RELATED APPLICATION

This application is a Continuation of U.S. Ser. No. 10/809,140, which was filed on Mar. 25, 2004 now abandoned.

This application claims priority to U.S. Provisional Application Ser. No. 60/457,735, filed on Mar. 25, 2003.

BACKGROUND OF THE INVENTION

The invention relates to a hydrogel string useful as a medical device and to a method for forming a hydrogel string. The method utilizes a device in which a prepolymer composition is brought into contact with a gelation initiator to form a hydrogel, which is then extruded from the device as the hydrogel string.

Hydrogels have been shown to be useful for a number of biomedical applications. For example, there are many instances in which an appropriate hydrogel biomaterial has been shown to be useful in repair of tissues and in augmentation of tissues, such as repair of defects and conditions in a tissue caused by disease, injury, or aging, repair of congenital defects and conditions in a tissue, and augmentation of tissues to provide a desirable functional, reconstructive, or cosmetic change. Bulking of the lower esophageal sphincter has been used for treatment of gastroesophageal reflux disease (GERD). Vesicoureteral reflux can be treated by endoscopic injection of a bulking agent in the submucosal space. Some types of incontinence can be treated by injection of a bulling agent into the submucosa of the urethra, in order to "beef up" the area and improve muscle tone. Spinal disc replacement or augmentation is another application where the use of hydrogels has been explored.

Another application for an appropriate hydrogel biomaterial is tissue embolization. Hydrogel embolic agents are useful for a variety of bioapplications, such as occluding blood vessels, occluding other body lumens such as fallopian tubes, filling aneurysm sacs, as arterial sealants, and as puncture sealants. Embolization of blood vessels is performed for a number of reasons, e.g. to reduce blood flow to and encourage atrophy of tumors, such as in the liver, to reduce blood flow and induce atrophy of uterine fibroids, for treatment of vascular malformations, such as arteriovenous malformations (AVMS) and arteriovenous fistulas (AVFs), to seal endoleaks into aneurysm sacs, to stop uncontrolled bleeding, or to slow bleeding prior to surgery.

Hydrogels have also been developed and used for drug delivery.

Hydrogel biomaterials can be preformed, such as hydrogel discs for drug delivery, or hydrogel microspheres for embolization. Hydrogels can also be formed in situ- at the site of embolization, for example. Each form has its advantages and disadvantages. Solid, preformed articles can be difficult to administer; larger articles can require invasive surgery and smaller articles can migrate after implantation. For example, solid particles and microspheres are generally unsuitable for filling aneurysms, particularly wide-necked aneurysms, due to migration of the particles or microspheres out of the sac.

Liquid, in situ formed materials can be flushed from the site during implantation. Another disadvantage is that the liquid may not form a cohesive solid mass, and bits of the hydrogel may be sloughed off over time.

Preformed polymeric strings have been proposed for use as biomaterials. U.S. Pat. No. 6,312,421 to Boock proposes preformed strings that are placed into a catheter for implantation. The strings are available in a set length, which reduces the flexibility of their use.

It would seem, therefore, that a hydrogel string that is formed at the time of delivery would be useful for many biomedical applications. The string would be available in the desired length, since it would be formed at the time of use.

SUMMARY OF THE INVENTION

Figure 1:
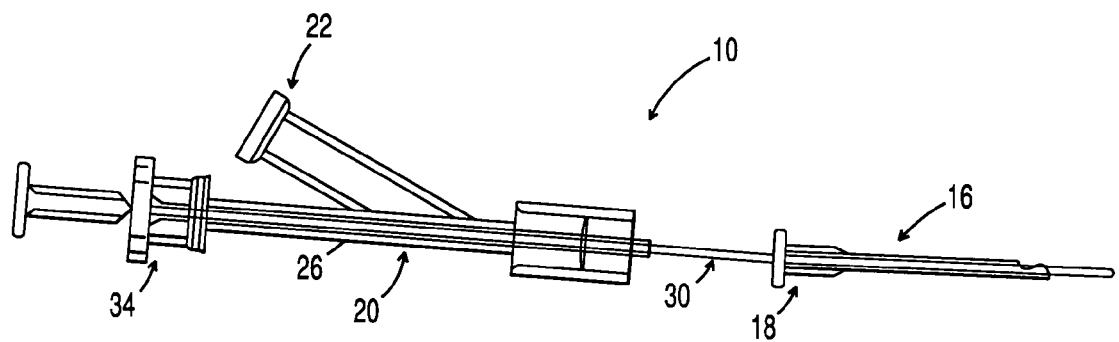
FIG. 1 is a schematic of one embodiment of the hydrogel string delivery device.

A hydrogel string that is useful as a medical device and a method for forming a hydrogel string that utilizes a delivery device in which gelation of a prepolymer is initiated to form a hydrogel, which is then extruded from the device as the hydrogel string.

DETAILED DESCRIPTION OF THE INVENTION

"Hydrogel" refers to a material having an aqueous phase with an interlaced polymeric component, with at least 10% to 90% of its weight as water.

"Macromer" means a crosslinkable macromonomer.

"Microcatheter" means a catheter having a distal tip size of about 4 French or smaller.

"Prepolymer" means a macromer or polymer composition that forms a hydrogel upon exposure to some initiation event.

In one aspect, the invention is a hydrogel string that is useful as a medical device. In another aspect, the invention is a method for forming a hydrogel string. The method utilizes a delivery device in which the hydrogel is formed within the device and extruded from the device at the intended site. The hydrogel can be formed in any manner, generally from a prepolymer that is brought into contact with an initiator within the device. The prepolymer component(s) are fed to the device from syringes or other reservoirs and the string can be formed and extruded having a length as long as desired. In one embodiment, the string is formed by bringing together two liquid components that form a hydrogel when combined in the device, and then extruding or pushing the string out of the device. In another embodiment, the string can be formed by having an initiator within the device, wherein the prepolymer contacts the initiator, the hydrogel forms, and is then extruded from the device. For example, the initiator could be part of the tip of a catheter.

In the preferred embodiment, the method involves bringing together two liquid components within a dual lumen catheter, having a mixing tip on the end. A variety of configurations of the two liquid components are possible. In one embodiment, the two liquid components may each contain prepolymer, whereupon the prepolymers form the hydrogel when mixed. In another embodiment, the two liquid components may each contain prepolymers and one or both components may contain a crosslinking initiator. In another embodiment, the prepolymer may be contained in only one component, while one or both components contain a crosslinking initiator. Or, the prepolymer may be in one component, while the initiator is in the other component. In any event, a hydrogel is formed when the components mix in the mixing tip.

The mixing and hydrogel formation is achieved within the lumen of the delivery catheter (or within the needle of a syringe). The hydrogel exits the catheter distal end as a string of fully or partially crosslinked hydrogel.

The Hydrogel Forming Components

The hydrogel string is formed from one or more prepolymers that can gel to form a hydrogel. Examples include hydrogels formed from macromers, as described in WO 01/68720 to BioCure, Inc. and U.S. Pat. No. 5,410,016 to Hubbell et al.

Gelation of the prepolymer can be via a number of mechanisms, such as physical crosslinking or chemical crosslinking. Physical crosslinking includes, but is not limited to, complexation, hydrogen bonding, desolvation, Van der wals interactions, and ionic bonding. Chemical crosslinking can be accomplished by a number of means including, but not limited to, chain reaction (addition) polymerization, step reaction (condensation) polymerization and other methods of increasing the molecular weight of polymers/oligomers to very high molecular weights. Chain reaction polymerization includes, but is not limited to, free radical polymerization (thermal, photo, redox, atom transfer polymerization, etc.), cationic polymerization (including onium), anionic polymerization (including group transfer polymerization), certain types of coordination polymerization, certain types of ring opening and metathesis polymerizations, etc. Step reaction polymerizations include all polymerizations which follow step growth kinetics including but not limited to reactions of nucleophiles with electrophiles, certain types of coordination polymerization, certain types of ring opening and metathesis polymerizations, etc. Other methods of increasing molecular weight of polymers/oligomers include but are not limited to polyelectrolyte formation, grafting, ionic crosslinking, etc.

Various crosslinkable groups are known to those skilled in the art and can be used, according to what type of crosslinking is desired. For example, hydrogels can be formed by the ionic interaction of divalent cationic metal ions (such as $Ca^{+2}$ and $Mg^{+2}$) with ionic polysaccharides such as alginates, xanthan gums, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, and amylopectin. Multifunctional cationic polymers, such as poly(1-lysine), poly(allylamine), poly(ethyleneimine), poly(guanidine), poly(vinyl amine), which contain a plurality of amine functionalities along the backbone, may be used to further induce ionic crosslinks.

Hydrophobic interactions are often able to induce physical entanglement, especially in polymers, that induces increases in viscosity, precipitation, or gelation of polymeric solutions. Block and graft copolymers of water soluble and insoluble polymers exhibit such effects, for example, poly(oxyethylene)-poly(oxypropylene) block copolymers, copolymers of poly(oxyethylene) with poly(styrene), poly(caprolactone), poly(butadiene), etc.

Other means for gelation also may be advantageously used with prepolymers that contain groups that demonstrate activity towards functional groups such as amines, imines, thiols, carboxyls, isocyanates, urethanes, amides, thiocyanates, hydroxyls, etc.

Desirable crosslinkable groups include (meth)acrylamide, (meth)acrylate, styryl, vinyl ester, vinyl ketone, vinyl ethers, etc. Particularly desirable are ethylenically unsaturated functional groups.

The method can be used to form a hydrogel string from any prepolymer system wherein a hydrogel can be formed by contacting the prepolymer with an initiator. For example, dual polymer systems such as that disclosed in U.S. Pat. No. 6,534,591 to Rhee et al. can be used.

The hydrogel can be formed from one or more macromers that include a hydrophilic or water soluble region and one or more crosslinkable regions. The macromers may also include other elements such as one or more degradable or biodegradable regions. A variety of factors—primarily the desired characteristics of the formed hydrogel—determines the most appropriate macromers to use. Many macromer systems that form biocompatible hydrogels can be used.

Macromers can be constructed from a number of hydrophilic polymers, such as, but not limited to, polyvinyl alcohols (PVA), polyethylene glycols (PEG), polyvinyl pyrrolidone (PVP), polyalkyl hydroxy acrylates and methacrylates (e.g. hydroxyethyl methacrylate (HEMA), hydroxybutyl methacrylate (HBMA), and dimethylaminoethyl methacrylate (DMEMA)), polysaccharides (e.g. cellulose, dextran), polyacrylic acid, polyamino acids (e.g. polylysine, polyethylmine, PAMAM dendrimers), polyacrylamides (e.g. polydimethylacrylamid-co-HEMA, polydimethylacrylamid-co-HBMA, polydimethylacrylamid-co-DMEMA). The macromers can be linear or can have a branched, hyperbranched, or dendritic structure.

Macromers suitable for use in the compositions described herein are disclosed in WO 01/68720 to BioCure, Inc. Other suitable macromers include those disclosed in U.S. Pat. No. 5,410,016 to Hubbell et al., U.S. Pat. No. 4,938,763 to Dunn et al., U.S. Pat. No. 5,100,992 and U.S. Pat. No. 4,826,945 to Cohn et al., U.S. Pat. No. 4,741,872 and U.S. Pat. No. 5,160,745 to De Luca et al, and U.S. Pat. No. 4,511,478 to Nowinski et al.

In a preferred embodiment, the macromers are those described in WO 01/68720 to BioCure, Inc. These macromers have a PVA backbone and at least two pendant chains containing ethylenically unsaturated groups that can be crosslinked. The crosslinkers are desirably present in an amount of from approximately 0.01 to 10 milliequivalents of crosslinker per gram of backbone (meq/g), more desirably about 0.05 to 1.5 meq/g.

The ethylenically unsaturated groups are crosslinked using a two part redox system. One part of the system contains a reducing agent such as a ferrous salt. Various ferrous salts can be used, such as, for example, ferrous gluconate dihydrate, ferrous lactate dihydrate, or ferrous acetate. The other half of the system contains an oxidizing agent such as hydrogen peroxide.

Other reducing agents can be used, such as, but not limited to, cuprous salts, cerous salts, cobaltous salts, permanganate, and manganous salts. Ascorbate, for example, can be used as a coreductant to recycle the reductant and reduce the amount needed. This can reduce the toxicity of a ferrous based system. Other oxidizing agents that can be used include, but are not limited to, t-butyl hydroperoxide, t-butyl peroxide, benzoyl peroxide, cumyl peroxide, etc.

The Delivery Device

The hydrogel string is formed within and delivered from a delivery device. Desirably, the device includes or is connected to a reservoir for the prepolymer, and includes the initiator. The device includes a mixing tip, or gelation tip, where the prepolymer contacts the initiator and forms the hydrogel. The device also includes a way to extrude the formed hydrogel out of the device. The preferred embodiment of the delivery device is a catheter. The catheter can be multilumen, especially if the initiator is provided via a second liquid.

In a preferred embodiment, a catheter having at least two lumens is employed in the method for forming the hydrogel string. A side-by-side dual lumen catheter can be used although a coaxial catheter is preferred. The distal portion of the catheter includes a gelation chamber of sufficient length for the two solutions to mix and form the hydrogel string. Preferably, one of the lumens or catheters is slidable within the mixing chamber, so that the length of the gelation chamber can be changed.

In one embodiment, the catheter is a coaxial dual lumen catheter, having a first, or outer, catheter and a second, or inner, catheter. The second catheter is positioned inside the first catheter to form a coaxial dual lumen catheter. The catheters are desirably used with a manifold, which provides for connection between the catheters and reservoirs that the two solutions are delivered from- such as syringes.

The device can further include a syringe holder, into which the syringes can be placed so that delivery of the two solutions can be synchronized. A guidewire can be used, if desired, to aid in placement of the catheters.

In one embodiment, illustrated by FIG. 1, the device 10 includes first catheter 16, which can be attached to the manifold 20 at its proximal end 18 via a luer adaptor 19, for example.

The manifold 20 includes a syringe adaptor 22 which provides connection (via a luer lock for example) between the interior space 26 of the manifold 20 (which leads into the first, outer catheter) and a syringe (not shown) for the first solution.

The second, inner, catheter 30 is sized so that it can be slid inside the first catheter 16. Furthermore, the second catheter should be sized to allow flow of a solution through the first catheter when the second catheter is in place. In other words, the second catheter should not fit too tightly within the first catheter.

The manifold 20 includes a second adaptor 34 to receive the second catheter 30. This can be a Tuohy-Borst adaptor, through which the second catheter can be inserted. The second catheter 30 is then pushed through the manifold and into and through the first catheter 16. Accordingly, the second solution delivered through the second catheter 30 does not contact the first solution delivered through the first catheter 16. A syringe (not shown) is fastened to the second catheter 30 for delivery of the second solution.

Figure 2:
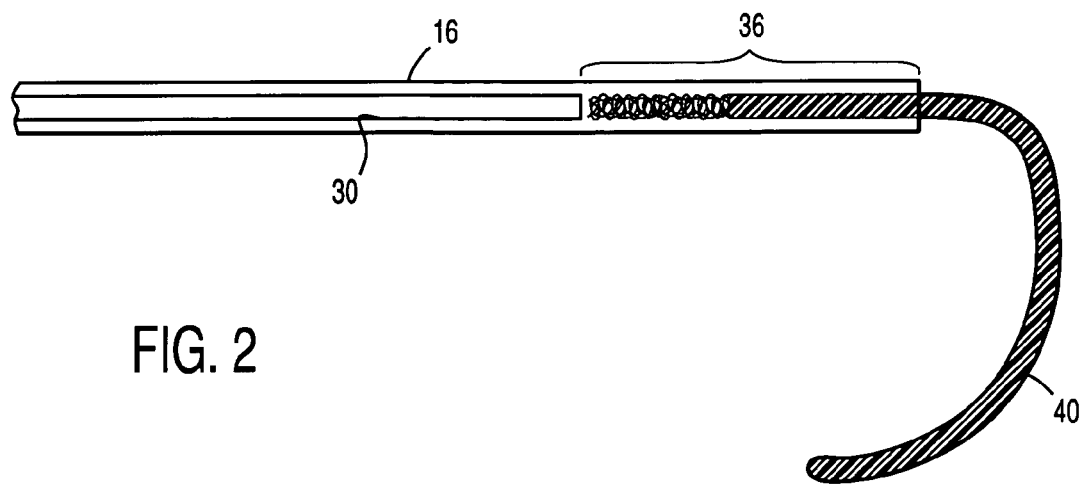
FIG. 2 is a schematic of the distal tip of one embodiment of the hydrogel string delivery device, showing the mixing chamber and the extruded hydrogel string.

As shown in FIG. 2, second catheter 30 terminates some distance before first catheter 16 so that gelation chamber 36 is formed at the distal end of first catheter 16. As the two solutions are combined in the gelation chamber 36, they form the hydrogel string 40.

If desired, the first and second syringes are retained within a syringe holder (not shown) which allows synchronized delivery of the two solutions. The manifold would desirably be designed so that the syringes are aligned.

For placement of the delivery device within the vasculature at the intended application site, a guidewire (not shown) can be used.

The first catheter can be a commercially available catheter, such as a FasTracker 325 or Tracker 18 microcatheter. It should be of appropriate size to access the intended site of application. The outer diameter of the first catheter therefore can be of any size, so long as it is appropriate for the application. The presently disclosed device is particularly applicable for neurovascular applications or site selective applications which, in some cases, require microcatheters down to 1.6 Fr or smaller. The practical upper limit to catheter size is about 8 Fr.

In one example, the first catheter can be a Tracker 18, having an inner diameter of 0.021 inches. The second catheter can have an outer diameter of 0.012 inches, and an inner diameter of 0.009 inches. The space between the first catheter's inner diameter and the second catheter's outer diameter can vary in size. The second catheter may be as small as about 0.7 Fr.

The first catheter can be made of standard catheter materials, typically a polymer such as, for example, polyurethane, polyethylene, silicone, or nylon. The second microcatheter can be made of a polymer but is desirably made of metal such as stainless steel or a binary nickel titanium alloy (nitinol). The second catheter can also be formed from standard catheter plastics but for use as a microcatheter is desirably formed from a metal, such as platinum, a platinum alloy, a nickel alloy, a titanium alloy, and some types of stainless steel (such as 316L stainless steel). Desirably, a binary nickel titanium alloy (nitinol) is used. Some plastics such as polyimide, polyethylene, polyurethane, and PTFE may be useful. The requirements for the fabrication material will depend upon the desired characteristics of the microcatheter, such as flexibility and strength, and the design parameters such as length and diameter. Desirably, medical grade superelastic nitinol is used.

The Method

The method for forming the hydrogel string is described with respect to filling an aneurysm but the method is applicable to a variety of biomedical applications. For example, the method and string can be used for repair of defects and conditions in a tissue caused by disease, injury, or aging, repair of congenital defects and conditions in a tissue, and augmentation of tissues to provide a desirable functional, reconstructive, or cosmetic change. Examples include bulking of the lower esophageal sphincter for treatment of gastroesophageal reflux disease (GERD), endoscopic injection of a bulking agent in the submucosal space to treat vesicoureteral reflux, treatment of incontinence by injection of a bulking agent into the submucosa of the urethra, in order to "beef up" the area and improve muscle tone, and replacement or augmentation of a spinal disc.

A variety of configurations of the two liquid components is possible. In one embodiment, the two liquid components may each contain prepolymer, whereupon the prepolymers form the hydrogel when mixed. In another embodiment, the two liquid components may each contain prepolymers and one or both components may contain a crosslinking initiator. In another embodiment, the prepolymer may be contained in only one component, while one or both components contain a crosslinking initiator. Or, the prepolymer may be in one component, while the initiator is in the other component.

In a preferred embodiment of the method, the coaxial dual lumen microcatheter described above is used. Since the inner diameter of the inner catheter is so small, the viscosity of the solution delivered through the inner catheter must be low. Solution containing macromer is delivered through the first (outer) catheter; and initiator solution is delivered through the second (inner) catheter. The initiator can be either reductant or oxidant and the other of the pair is delivered with the macromer. Liquid contrast agent can be contained in both solutions.

Using the microcatheter described above, the first (outer) catheter is positioned at the administration site, desirably using a guidewire. The second (inner) catheter is threaded through the first catheter (first removing the guidewire if one has been used). The first and second catheters are connected to syringes or other dispensers holding the two solutions (as described above). The catheters may be part of a delivery device including a manifold and syringe holder, if desired. The method then involves delivering the two solutions which gel in the catheter gelling chamber.

The nature of the string 40 in the gelation chamber 36 changes through the length of the gelation chamber 36. At the proximal end of the chamber, the solutions are first coming into contact and begin to mix. Initiation of gelation begins and the string begins to form. As shown in FIG. 2, the composition is liquid at the proximal end and gelled at the distal end. Further injection of solutions into the catheters force the string out of the distal tip of the catheter and into the aneurysm, for example.

Desirably, the inner catheter is slidable within the outer catheter. If the operator wants to inject a less gelled composition into the aneurysm, he can slide the inner catheter towards the distal end of the gelation chamber, which means the composition exiting the catheter will be less solid. This may be desirable, for example, in order to fill in the spaces.

The method can deliver a composition ranging from a distinct solid string to a semi-solid near liquid.

The gelation time of the compositions can be varied from about 0.5 seconds to as long as 10 minutes, and longer if desired. The gelation time will generally be affected by, and can be modified by changing at least the following variables: the initiator system, crosslinker density, macromer molecular weight, macromer concentration (solids content), and type of crosslinker. A higher crosslinker density will provide faster gelation time; a lower molecular weight will provide a slower gelation time. A higher solids content will provide faster gelation time. For redox systems the gelation time can be designed by varying the concentrations of the redox components. Higher reductant and higher oxidant will provide faster gelation, higher buffer concentration and lower pH will provide faster gelation.

The firmness of the formed hydrogel will be determined in part by the hydrophilic/hydrophobic balance, where a higher hydrophobic percent provides a firmer hydrogel. The firmness will also be determined by the crosslinker density (higher density provides a firmer hydrogel), the macromer molecular weight (lower MW provides a firmer hydrogel), and the length of the crosslinker (a shorter crosslinker provides a firmer hydrogel).

The swelling of the hydrogel is inversely proportional to the crosslinker density. Generally, no or minimal swelling is desired, desirably less than about 10 percent.

Elasticity of the formed hydrogel can be increased by increasing the size of the backbone between crosslinks and decreasing the crosslinker density. Incomplete crosslinking will also provide a more elastic hydrogel. Preferably the elasticity of the hydrogel substantially matches the elasticity of the tissue to which the composition is to be administered.

Contrast Agents

It may be desirable to include a contrast agent in the hydrogel string. A contrast agent is a biocompatible (non-toxic) material capable of being monitored by, for example, radiography. The contrast agent can be water soluble or water insoluble. Examples of water soluble contrast agents include metrizamide, iopamidol, iothalamate sodium, iodomide sodium, and meglumine. Iodinated liquid contrast agents include Omnipaque®, Visipaque®, and Hypaque-76®. Examples of water insoluble contrast agents are tantalum, tantalum oxide, barium sulfate, gold, tungsten, and platinum. These are commonly available as particles preferably having a size of about 10 µm or less.

The contrast agent can be added to one or both of the solutions prior to administration. Both solid and liquid contrast agents can be simply mixed with one or both solutions. Liquid contrast agent can be mixed at a concentration of about 10 to 80 volume percent, more desirably about 20 to 50 volume percent. Solid contrast agents are desirably added in an amount of about 10 to 40 weight percent, more preferably about 20 to 40 weight percent.

Active Agents

An effective amount of one or more biologically active agents can be incorporated into the hydrogel string simply by including the agent in one or both solutions. It may be desirable to deliver the active agent from the formed hydrogel. Biologically active agents that it may be desirable to deliver include prophylactic, therapeutic, and diagnostic agents including organic and inorganic molecules and cells (collectively referred to herein as an "active agent" or "drug"). A wide variety of active agents can be incorporated into the hydrogel. Release of the incorporated additive from the hydrogel is achieved by diffusion of the agent from the hydrogel, degradation of the hydrogel, and/or degradation of a chemical link coupling the agent to the polymer. In this context, an "effective amount" refers to the amount of active agent required to obtain the desired effect.

Examples of active agents that can be incorporated include, but are not limited to, anti-angiogenic agents, chemotherapeutic agents, radiation delivery devices, such as radioactive seeds for brachytherapy, and gene therapy compositions.

Chemotherapeutic agents that can be incorporated include water soluble chemotherapeutic agents, such as cisplatin (platinol), doxorubicin (adriamycin, rubex), or mitomycin C (mutamycin). Other chemotherapeutic agents include iodinated fatty acid ethyl esters of poppy seed oil, such as lipiodol.

Cells can be incorporated into the compositions, including cells to encourage tissue growth or cells to secrete a desired active agent. For example, cells that can be incorporated include fibroblasts, endothelial cells, muscle cells, stem cells, etc. Cells can be modified to secrete active agents such as growth factors.

Active agents can be incorporated into the compositions simply by mixing the agent with one or both solutions. The active agent will then be entrapped in the hydrogel string. The active agent can be in compound form or can be in the form of degradable or nondegradable nano or microspheres. It some cases, it may be possible and desirable to attach the active agent to the macromer. The active agent may be released from the macromer or hydrogel over time or in response to an environmental condition.

Other Additives

It may be desirable to include a peroxide stabilizer in redox initiated systems. Examples of peroxide stabilizers are Dequest® products from Solutia Inc., such as for example Dequest® 2010 and Dequest® 2060S. These are phosphonates and chelants that offer stabilization of peroxide systems. Dequest® 2060S is diethylenetriamine penta(methylene phosphonic acid). These can be added in amounts as recommended by the manufacturer.

It may be desirable to include fillers in the compositions, such as fillers that leach out of the formed hydrogel over a period of time and cause the hydrogel to become porous. Such may be desirable, for example, where the composition is used for chemoembolization and it may be desirable to administer a follow up dose of chemoactive agent. Appropriate fillers include calcium salts, for example.

The examples below serves to further illustrate the invention, to provide those of ordinary skill in the art with a complete disclosure and description of how the compounds, compositions, articles, devices, and/or methods claimed herein are made and evaluated, and is not intended to limit the scope of the invention. In the examples, unless expressly stated otherwise, amounts and percentages are by weight, temperature is in degrees Celsius or is at ambient temperature, and pressure is at or near atmospheric. The examples are not intended to restrict the scope of the invention.

EXAMPLE 1

Two prepolymer solutions were formulated as follows. Each solution was individually weighed or dispensed into a 20 ml scintillation vial furnished with a magnetic stirrer bar then stirred until homogeneous. The solutions were then allowed to stand to allow any resulting air bubbles to dissipate.

Part A:

| | |
|---|---|
| 30% Acrylamide functionalized PVA macromer | 2.33 g |
| 50% 2-acrylamido-2-methylpropane sulphonate, sodium salt (pH 8) | 0.60 g |
| Omnipaque 350 | 5.00 g |
| 415 mM Hydrogen peroxide | 500 uL |
| Deionized water | 1.57 g |

Part B:

| | |
|---|---|
| 50% 2-acrylamido-2-methylpropane sulphonate, sodium salt (pH 8) | 2.00 g |
| Omnipaque 350 | 5.00 g |
| 83 mM Fe(II) lactate | 1.50 g |
| 415 mM Ascorbic acid | 0.20 g |
| Deionized water | 1.30 g |

The prepolymer solutions Part A and Part B were delivered via a coaxial microcatheter system. A Touy-Borst Y-connect was attached to a FasTracker 325 microcatheter (Boston Scientific, Target; Length=125 cm) then flushed with saline. A nitinol catheter (length=165 cm, o.d.=0.012 inches) with a spiral cut tip was preflushed with saline and inserted into the microcatheter via the Y-connector. Once the tip of the nitinol catheter was approximately 10 cm behind the tip of the microcatheter it was secured in place with the Y-connector.

Solution Part A was drawn up in a mL Luer-Lok syringe then attached to the Y-connector. The thread on the Y-connector (used to lock the nitinol catheter in place) was loosened. The Y-connector was then back flushed with solution Part A to replace the saline (which was expelled via the loosened top thread of the Y-connector). Once the saline was exchanged, the thread on the Y-connector was retightened and injection of solution Part A was continued to allow flushing of the microcatheter. Once this was completed the syringe was removed and refilled. The syringe was attached to a hand torque syringe delivery device then reattached to the Y-connect being careful to avoid the formation of air bubbles.

The nitinol catheter was flushed with saline using a Luer-Lok syringe. Solution Part B was then drawn up in a new mL Luer-Lok syringe, attached to the nitinol catheter and finally to the hand torque syringe delivery device which allowed controlled quantities of solutions Part A and B to be delivered simultaneously.

Solutions Part A and B were slowly injected through the catheters. Upon the two solutions contacting in the tip of the microcatheter hydrogel formation was initiated. The resulting polymer exited the tip of the microcatheter in a string or thread like form equal in diameter to the internal diameter of the microcatheter.

EXAMPLE 2

The two pre-polymer solutions were formulated as follows. Each solution was individually weighed or dispensed in to a 20 ml scintillation vial furnished with a magnetic stirrer bar then stirred until homogeneous. The solutions were then allowed to stand to allow any resulting air bubbles to dissipate.

Part A:

| | |
|---|---|
| 30% Acrylamide functionalized PVA macromer | 3.00 g |
| Acryloxyethyl trimethylammonium chloride (80%) | 0.38 g |
| Omnipaque 350 | 6.10 g |
| 415 mM Hydrogen peroxide | 500 uL |

Part B:

| | |
|---|---|
| 30% Acrylamide functionalized PVA macromer | 0.67 g |
| Acryloxyethyl trimethylammonium chloride (80%) | 1.25 g |
| Omnipaque 350 | 6.35 g |
| 83 mM Fe(II) lactate | 1.50 g |
| 415 mM Ascorbic acid | 0.20 g |

A similar delivery device was used as in Example 1. The outer catheter was a 2.5 Fr Renegade microcatheter (Boston Scientific, Target; length=150 cm). The inner catheter was a nitinol catheter (length 175 cm, o.d. 0.012 inches) with a spiral cut tip. The mixing chamber was about 6 cm.

As in example 1, a hydrogel string having approximately the diameter of the delivery device outer catheter was extruded from the device.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A method for augmentation or replacement of biological tissue, comprising injecting a hydrogel string to augment or replace the tissue, wherein the hydrogel string is formed and delivered using a device that has a gelation chamber in which a prepolymer is crosslinked to form a folly crosslinked hydrogel and from which the fully crosslinked formed hydrogel is extruded as a hydrogel string;

wherein the prepolymer comprises two solutions, where one solution includes one component of a redox couple and the other solution includes the other component of the redox couple, and where at least one of the solutions includes macromers having a PVA backbone and at least two pendant chains bearing crosslinkable groups; and wherein the device is a coaxial microcatheter having an inner catheter slidable within an outer catheter, wherein the inner catheter does not extend all the way to the distal end of the outer catheter so that a gelation chamber is formed at the distal end of the outer catheter, wherein the hydrogel string is extruded from the catheter as prepolymer is moved into the gelation chamber, and wherein the distal tip of the outer catheter is substantially the same diameter as the gelation chamber.

2. The method of claim 1, wherein the method is used to bulk tissue for therapeutic or cosmetic purposes, for embolization, to augment the lower esophageal sphincter to treat gastroesophageal reflux disease (GERD), augment the submucosal space to treat vesicoureteral reflux, augment the submucosa of the urethra to treat incontinence, or to augment or replace a spinal disc.

3. The method of claim 1, wherein the method is used for embolization.

4. The method of claim 1, wherein the method is used to block passage through fallopian tubes.

5. The method of claim 1, wherein the method is used to augment or replace a spinal disc.

6. The method of claim 1, wherein the method further comprises the additional step of sliding the inner catheter within the outer catheter to decrease the length of the gelation chamber and the degree of gelation of the hydrogel, and delivering an incompletely crosslinked hydrogel to the tissue and filling in the spaces.

7. The method of claim 1 wherein the prepolymer includes a contrast agent or active agent.

8. A method for augmentation or replacement of biological tissue, comprising injecting a hydrogel string to augment or replace the tissue, wherein the hydrogel string is formed and delivered using a catheter that has a gelation chamber in which a prepolymer is crosslinked to form a fully crosslinked hydrogel, wherein the catheter has a distal tip which is substantially the same diameter as the gelation chamber, and from which the formed hydrogel is extruded as a hydrogel string, and wherein the degree of gelation of the hydrogel can be controlled; wherein the prepolymner comprises two solutions, where one solution includes one component of a redox couple and the other solution includes the other component of the redox couple, and wherein at least one of the solutions includes macromers having a PVA backbone and at least two pendant chains bearing crosslinkable groups.

* * * * *